(12) United States Patent
Robinson et al.

(10) Patent No.: US 10,220,128 B1
(45) Date of Patent: Mar. 5, 2019

(54) IMPLANTED CARDIAC DEVICE TO TREAT HEART FAILURE

(76) Inventors: Allan R. Robinson, Minneapolis, MN (US); Theodore J. Lillehei, Minneapolis, MN (US)

( * ) Notice: Subject to any disclaimer, the term of this patent is extended or adjusted under 35 U.S.C. 154(b) by 1227 days.

(21) Appl. No.: 12/590,378

(22) Filed: Nov. 6, 2009

Related U.S. Application Data

(60) Provisional application No. 61/198,455, filed on Nov. 6, 2008.

(51) Int. Cl.
*A61M 1/10* (2006.01)

(52) U.S. Cl.
CPC .................................. *A61M 1/1037* (2013.01)

(58) Field of Classification Search
CPC .................................................... A61M 1/1037
USPC ................................................ 600/16–18, 37
See application file for complete search history.

(56) References Cited

U.S. PATENT DOCUMENTS

| | | | |
|---|---|---|---|
| 5,607,385 A | 3/1997 | Francischelli | |
| 6,193,648 B1 | 2/2001 | Krueger | |
| 6,406,421 B1 | 6/2002 | Grandjean | |
| 6,595,912 B2 | 7/2003 | Lau | |
| 6,896,652 B2 | 5/2005 | Alferness | |
| 7,097,611 B2 | 8/2006 | Lau | |
| 7,155,295 B2 | 12/2006 | Lau | |
| 7,198,594 B2 | 4/2007 | Shahinpoor | |
| 7,291,105 B2 | 11/2007 | Lau | |
| 7,381,181 B2 | 6/2008 | Lau | |
| 2003/0212306 A1 | 11/2003 | Banik | |
| 2004/0010180 A1 | 1/2004 | Scorvo | |
| 2004/0249236 A1 | 12/2004 | Hedge | |
| 2005/0004428 A1 | 1/2005 | Cox | |
| 2005/0255592 A1 | 11/2005 | Collins | |
| 2006/0142634 A1* | 6/2006 | Anstadt et al. | 600/16 |
| 2006/0211909 A1 | 9/2006 | Anstadt | |
| 2007/0021652 A1* | 1/2007 | Lau et al. | 600/37 |
| 2007/0197859 A1* | 8/2007 | Schaer et al. | 600/37 |
| 2008/0116764 A1 | 5/2008 | Heim | |

OTHER PUBLICATIONS

Bar-Cohen, 2008, Electroactive polymer actuators and sensors. MRS Bulletin 33:173-177.
Smela, 2008, Conjugated polymer actuators. MRS Bulletin 33:197-204.

(Continued)

*Primary Examiner* — Eric D. Bertram
(74) *Attorney, Agent, or Firm* — Hugh Mctavish

(57) ABSTRACT

New methods and devices for treating heart failure and other cardiac disease conditions. Devices include a cardiac jacket adapted to fit generally around at least a portion of the heart. The jacket in some embodiments includes an electroactive polymer to squeeze the exterior of the heart to assist contraction of one or more pumping chambers, preferably the left ventricle. The jacket may also include stem cells on an inner surface of the jacket. The stem cells differentiate into cardiac tissue and help treatment of heart failure. Some embodiments also involve delivering an electric field or an electric current to electrically conductive material in the jacket to establish an electromagnetic field at the surface of the heart effective to promote growth and differentiation of stem cells into cardiac tissue.

10 Claims, 5 Drawing Sheets

(56) References Cited

OTHER PUBLICATIONS

Park, 2008, Physical propertios of ionic polymer-metal composites . . . MRS Bulletin 33:190-195.
Calvert, 2008, Gel sensors and actuators. MRS Bulletin 33:207-212.
Taylor, DA. 1998, Regenerating functional myocardium, Nature Medicine 4:929-933.

\* cited by examiner

IMPLANTED CARDIAC DEVICE TO TREAT HEART FAILURE

This application claims priority under 35 U.S.C. § 119(e) from U.S. provisional patent application Ser. No. 61/198,455, filed Nov. 6, 2008.

BACKGROUND

Congestive heart failure is a debilitating and progressive disease that causes a heart to pump less efficiently over time. Typically, the heart has been weakened by an underlying problem, such as clogged arteries, high blood pressure, a defect in heart muscles or heart valves, or some other medical condition. Many symptoms and conditions associated with heart failure can be treated, but to date in many cases the underlying impairment of the heart cannot.

One characteristic of heart failure is remodeling of the heart—that is, physical change to the size and shape of the heart and thickness of the heart wall. In many cases the wall of the left ventricle thins and stretches in places. The thinned portion of the myocardium is typically functionally impaired and other portions may grow or thicken to compensate.

Typically, the heart enlarges as heart failure progresses, which seems to be the result of the body trying to compensate for weakening heart muscles. The heart can become so enlarged that the heart can no longer provide an adequate supply of blood to the body. As a result, individuals afflicted with congestive heart failure often experience shortness of breath and fatigue even with minimal activity. Also, as the heart enlarges, the heart valves may not adequately close, which further reduces the heart's ability to supply blood to the body.

Drug therapies have been developed to treat individuals afflicted with congestive heart failure. A drug regimen of beta blockers, diuretics, and angiotensin-converting enzyme inhibitors (ACE inhibitors) aims to improve the effectiveness of the heart's contractions and slow CHF progression. Although drug therapy for heart failure can improve the quality of life and also modestly prolong survival, it is well established that many of the currently available approaches do not represent satisfactory long-term treatment options for a large number of patients.

Once the disease progresses to the point that medication is no longer effective, the currently preferred options are a heart transplant or a ventricular assist device (VAD). Approximately 550,000 new cases of CHF are diagnosed in the United States alone every year. Of these, at least 75,000 individuals are candidates for a heart transplant. But more than 50,000 men and women die every year waiting for a heart transplant because of a lack of donor hearts.

Only a few hundred VADs are implanted in the US each year. VAD use is limited because device implant surgery is highly invasive and complicated. Management of pump volume or pressure is difficult. VAD surgery adds insult to the heart because of the required surgical connections into the ventricle and aorta. But the largest contributor to complications from VAD implantation is the required direct interface of the device with the patient's blood. This can lead to clotting, strokes, and infection.

In addition to drugs, transplants, and VADs, heart failure has been treated with cardiac jackets or restraint devices. These basically consist of flexible material wrapped around the heart. A cardiac jacket is fitted around an enlarged heart to physically limit expansion of the heart during diastole. This may prevent further enlargement of the heart.

Improved methods and devices for treating heart failure and other cardiac diseases are needed.

SUMMARY

The embodiments of the invention are directed to new methods and devices for treating heart failure and other cardiac disease conditions.

One embodiment of the invention provides a device for treating cardiac disease comprising: a cardiac jacket adapted to fit generally around at least a portion of the heart, the jacket comprising an electroactive polymer (EAP) and the jacket having an inner surface in contact with the heart wall and an outer surface; and stem cells adhering to or entrapped on the inner surface of the cardiac jacket. The EAP switches between a longer and shorter state in response to electrical activation. The EAP is arranged in the jacket such that when it is in the shorter state it contracts circumference of the cardiac jacket about the heart so as to assist contraction of one or more pumping chambers of the heart.

Another embodiment of the invention provides a method of treating cardiac disease comprising: (a) implanting in a patient a cardiac jacket adapted to fit generally around at least a portion of the heart, the jacket comprising electrically conductive material; and (b) electrically linking the electrically conductive material of the cardiac jacket to a generator; wherein the generator is adapted to deliver an electric potential or an electric current to the electrically conductive material to establish an electromagnetic field at the surface of the heart effective to promote growth and differentiation of the stem cells into cardiac tissue.

Another embodiment provides a device for treating cardiac disease comprising: (a) a cardiac jacket adapted to fit generally around at least a portion of the heart, the jacket comprising electrically conductive material; (b) a generator electrically linked by (c) electrical leads to (d) the electrically conductive material of the cardiac jacket; wherein the generator is adapted to deliver an electric potential or an electric current to the electrically conductive material to establish an electromagnetic field at the surface of the heart effective to promote growth and differentiation of the stem cells into cardiac tissue.

Another embodiment of the invention provides a device for treating cardiac disease comprising: (a) a cardiac jacket adapted to fit generally around at least a portion of the heart, the jacket comprising an electrically conductive material and one or more bladders adapted for dilation and contraction in response to varying fluid pressure therewithin; (b) a fluid pump; (c) conduits connecting the one or more bladders and the fluid pump; wherein the one or more bladders are adjacent a pumping chamber of the heart to exert varying mechanical pressure on a region of the pumping chamber of the heart with dilation and contraction of the one or more bladders; and (d) a generator electrically linked by electrical leads to the electrically conductive material of the cardiac jacket; wherein the generator is adapted to deliver an electric potential or an electric current to the electrically conductive material to establish an electromagnetic field at the surface of the heart effective to promote growth and differentiation of the stem cells into cardiac tissue.

A method of treating cardiac disease comprising: (a) implanting in a patient a cardiac jacket adapted to fit generally around at least a portion of the heart, the jacket comprising an electroactive polymer, wherein the electroactive polymer switches between a longer and shorter state in response to electrical activation; wherein the electroactive polymer is arranged in the jacket such that when the electroactive polymer is in the shorter state it contracts circumference of the cardiac jacket about the heart so as to assist contraction of one or more pumping chambers of the heart; and (b) delivering stem cells to the heart of the patient.

DETAILED DESCRIPTION

Figure 1:
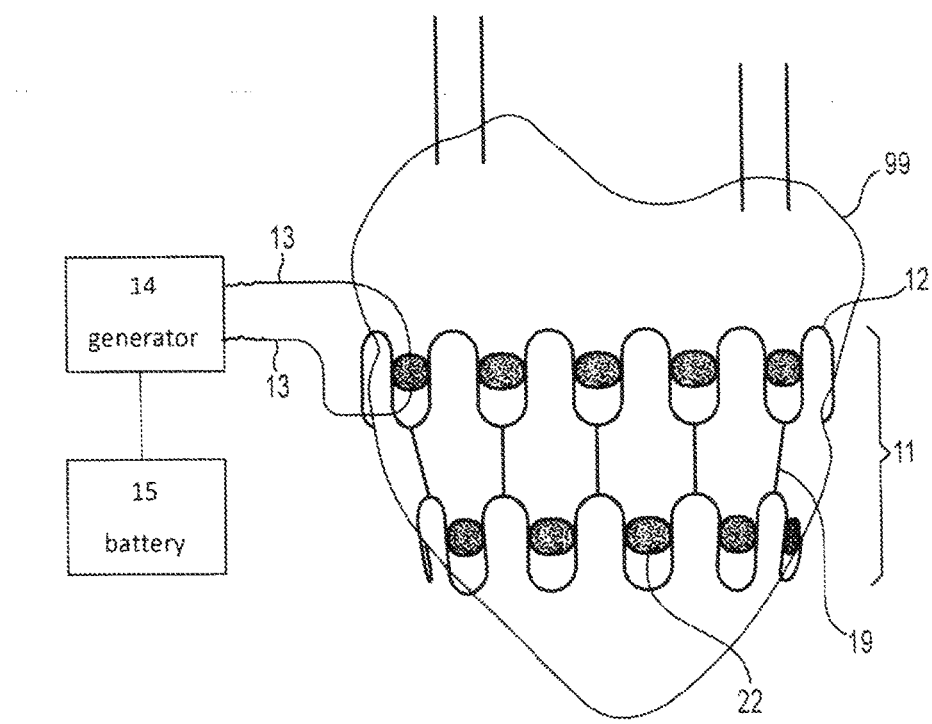
FIG. 1 shows an embodiment of the invention of a device for treating cardiac disease comprising a cardiac jacket. The jacket includes an electroactive polymer.
Figure 2:
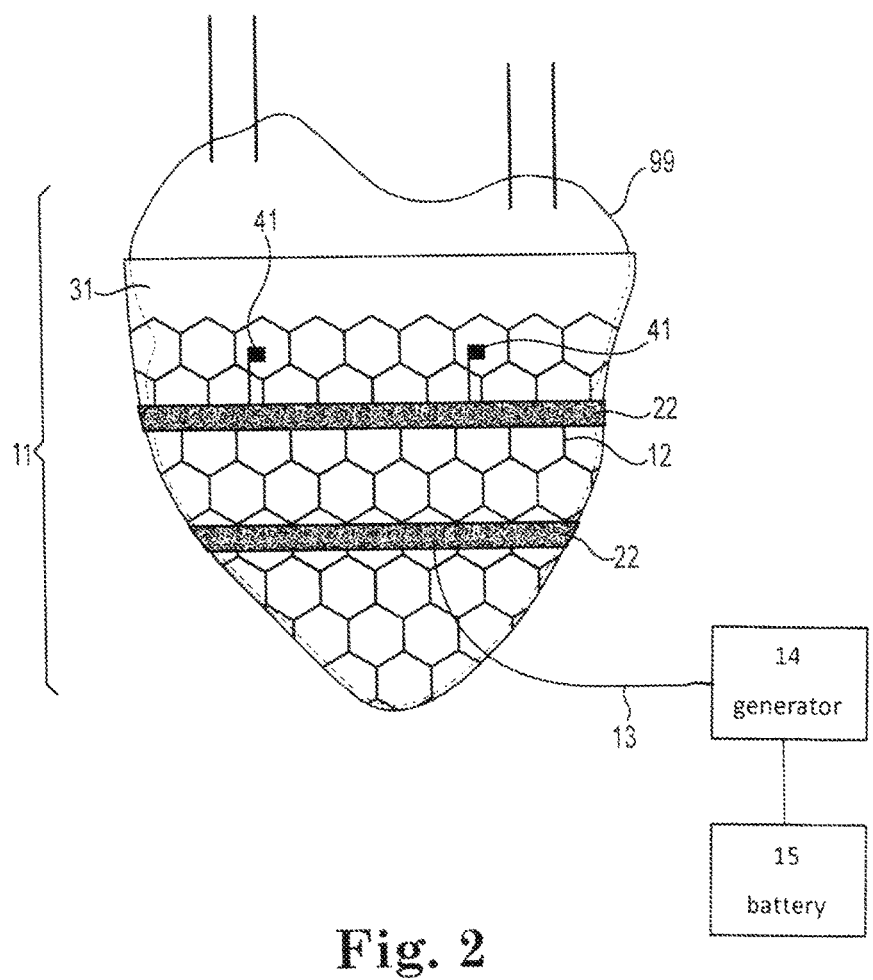
FIG. 2 shows another embodiment of the invention of a device for treating cardiac disease comprising a cardiac jacket. The jacket includes an electroactive polymer, as well as an inner liner that can be seeded with stem cells, and dimensional transducer elements for monitoring expansion and contraction of the heart and cardiac jacket.

Embodiments of the invention provide a device for treating cardiac disease comprising a cardiac jacket adapted to fit generally around at least a portion of the heart and methods of using the devices to treat cardiac disease. Examples of jackets 11 are shown in FIGS. 1 and 2.

The jackets typically circumscribe the ventricles and the lower half of the heart. The jackets restrict expansion of the heart in diastole, which restricts further enlargement of the heart in heart failure.

The jackets are preferably flexible. They may comprise, for instance, fabric, nitinol, or polymers. The jacket is preferably flexible enough to substantially conform to the shape of the heart.

In some embodiments, the jackets include interconnected rows or strands of an undulating (e.g., sinusoidally shaped) metal (e.g., stainless steel or nitinol) (U.S. Pat. No. 7,155,295). A strand 12 of undulating metal is shown in FIG. 1.

In particular embodiments, the jacket includes an elastic material. An elastic material is defined herein as a material that deforms reversibly under stress. The elasticity may be true elasticity, due to stretching of bonds, or pseudoelasticity (a characteristic of, for example, nitinol).

The jacket may include a biologically inert material. Examples of suitable biologically inert materials include polypropylene, polyester, silicone rubber, nitinol and stainless steel.

In some embodiments, the jacket comprises material, preferably the inner surface (the surface facing the heart) of the jacket, that is a good substrate for tissue growth so that tissue from the heart adheres to the jacket, locking the jacket in place against the heart. Most polyurethanes, for instance, are substantially non-biodegradable and good substrates for tissue growth. Many other substrates that allow or facilitate tissue attachment are also known to persons of skill in the art. Thus, in some embodiments, the jacket is adapted to adhere to the heart wall through tissue growth. The tissue growth may be from stem cells implanted in the patient (e.g., adhering to or entrapped in the inner surface of the jacket) or from other cells native to the patient (e.g., growth from the heart wall). FIG. 2 shows a jacket 11 that includes inner liner 31 that may be seeded with stem cells.

In other embodiments, the jacket is sewn or mechanically attached to the heart wall at one or more points. Where the jacket is attached to the heart wall, either through tissue growth or mechanically, and the jacket includes an EAP, the expansion of the EAP can serve to assist with expansion of one or more heart pumping chambers during diastole, as well as contraction of the EAP assisting with contraction of one or more heart pumping chambers in systole.

Thus, in some embodiments, the jacket comprising an EAP assists expansion of one or more pumping chambers of the heart in diastole. In other embodiments, the jacket comprising an EAP assists contraction of one or more pumping chambers of the heart in systole. In other embodiments, the jacket comprising an EAP assists both expansion and contraction of one or more pumping chambers of the heart. In FIG. 1, EAP 22 is shown linking two segments of the same sinusoidally shaped strand 12 of electrically conductive material. Contraction of the EAP 22 reduces the circumference of the strand of material 12 and jacket 11 to help contract the heart.

In some embodiments, the jacket comprises an electroactive polymer. The electroactive polymer is preferably activated electrically in use to constrict the jacket to squeeze one or both ventricles of the heart to assist pumping by the heart. The electroactive polymer must contract in rhythm with the natural rhythm of the heart, i.e., at about 40 to 120 contractions per minute at rest. It only needs to assist the natural contraction of the heart. So any amount of constriction of the jacket by the EAP is helpful. Preferably contraction of the EAP reduces the circumference of the jacket by 5-20%.

In these embodiments, the device preferably further comprises a computerized generator 14 linked by one or more electrical leads 13 to the electroactive polymer of the cardiac jacket.

The generator 14 may be linked to any suitable power source. But preferably the device includes a battery 15 electrically coupled to the generator. With a battery, the device can be entirely implanted, and the patient is not tethered to any external components and can move on his own. Having all components of the device internal to the patient also reduces the risk of infection.

The computerized generator, battery, and electrical leads essentially are a pacemaker. The pacemaker stimulates the electroactive polymers to stimulate contraction of the polymers, which assists contraction of the heart. The pacemaker may also stimulate the heart in coordination with stimulating the EAP, in which case the pacemaker includes one or more electrical leads linking the generator to one or more electrodes contacting cardiac muscle of one or more pumping chambers of the heart to pace pumping of the heart muscle. The pacemaker is preferably rate responsive. That is, the rate of pacing is responsive to physiological signals, including the patient's natural heart rate or breathing rate, or responsive to movement of the patient.

Thus, in one embodiment, the device includes one or more sensing electrodes electrically coupled to the heart and electrically coupled to the computerized generator, wherein the device is adapted to detect the contraction rhythm of the heart (electrical signals produced by the heart) with the sensing electrodes and to generate electrical pulses effective to contract the EAP with the computerized generator at a variable rate responsive to physiological activity of the patient. The sensing electrodes may be the same electrodes as the electrodes contacting cardiac muscle of one or more pumping chambers of the heart to pace pumping of the heart muscle.

In other embodiments where the pacemaker is rate-responsive, the device includes an accelerometer to detect movement of the patient. Detection of movement of the patient, rather than electrical signals produced by the heart, in these embodiments may be used to alter the rhythm of the pacemaker.

In some embodiments, the device comprises one or more electrical leads linking the generator to one or more electrodes contacting cardiac muscle of one or more pumping chambers of the heart to pace pumping of the heart.

The pacemaker in some embodiments is a biventricular pacemaker. Biventricular pacing has been shown to be beneficial to some heart failure patients. Thus, in some embodiments the device comprises electrical leads linking the generator to an electrode contacting cardiac muscle of the left ventricle and an electrode contacting cardiac muscle of the right ventricle to coordinately pace both ventricles.

The devices may also include an implantable cardioverter defibrillator comprising: (a) a capacitor for storing electrical charge, linked by (b) electrical leads to (c) at least two electrodes contacting tissue, wherein at least one of the electrodes contacts cardiac tissue.

In particular embodiments, the cardiac jacket includes an electrically conductive material. The electrically conductive material can be the EAP itself, in the case of an ionic conjugated polymer actuator EAP, such as a polypyrole. It can be a material separate from the EAP. The electrically conductive material can serve as an electrode for the EAP. The electrically conductive material can also function to allow delivery of an electromagnetic field to the surface of the heart through the EAP to stimulate tissue growth in the heart.

In some embodiments, the jacket comprises an electrically conductive material but does not comprise an EAP.

In some embodiments where the jacket includes an EAP and an electrically conductive material separate from the EAP, the electrically conductive material is linked electrically and mechanically to the EAP.

In one embodiment, the electrically conductive material is formed into one or more undulating (e.g., sinusoidally shaped) strands arranged laterally on the heart, wherein the electroactive polymer links portions of the same or different sinusoidally shaped strands.

In one embodiment, the strands of electrically conductive material form one or more bands completely circumscribing the heart.

The device typically includes electrical leads electrically linking the generator and the electrically conductive material.

In one embodiment, the EAP 22 links together undulations of ribbons of another material 12 in the jacket, such as is shown in FIG. 1. Where the undulating ribbons are composed of an electrically conductive material, the undulating ribbons can also serve as electrodes for the EAP. In this case, each segment of EAP may link to two separate ribbons of electrically conductive material to provide cathode and anode electrodes for the EAP. Alternatively, each segment of the EAP may link only to one segment of the electrically conductive material of the jacket, in which case the electrically conductive material of the jacket can serve as one electrode and adjoining tissue of the body, e.g., cardiac tissue, can serve as the other electrode or ground.

Figure 3:
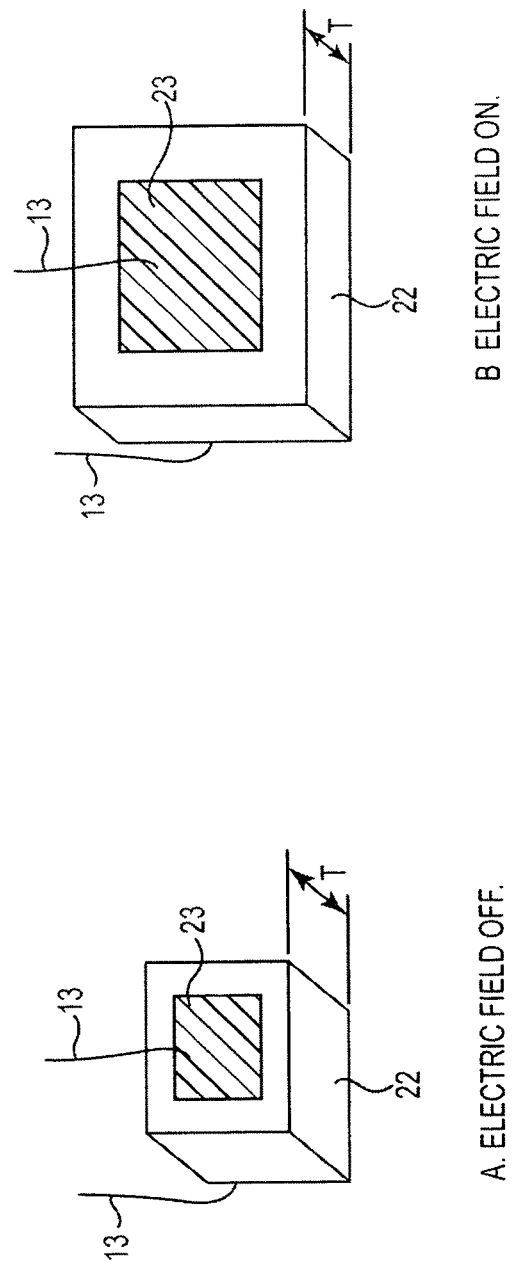
FIG. 3 shows expansion of a field-activated electroactive polymer with application of an electric field. In panel A, no electric field is applied and the electroactive polymer is thicker. In panel B, an electric field is applied causing the electroactive polymer to become thinner and correspondingly longer and wider.

The EAP may be in specific embodiments, a field-activated EAP or an ionic EAP (1). Field-activated EAPs include silicone, polyurethane, polyvinylidene fluoride (PVDF), and VHB 4910 (3M, Oakdale, Minn.). Those are dielectric EAPs. In these, applying a charge to electrodes on opposite surfaces of the EAP causes the EAP to become thinner, which in turn lengthens the EAP to conserve the total volume. The lengthening with application of an electric field and shortening with removal of the electric field is harnessed to expand and contract a dimension of the cardiac jacket. This is shown in FIG. 3. EAP 22 has electrodes 23 on the top and bottom surfaces of the EAP in FIG. 3. The electrodes are linked by electrical leads 13 to a generator to apply an electric field across the EAP 22. The EAP 22 has a thickness T. In panel A, the EAP is at rest. In FIG. 3 panel B, when the electric field is applied to the electrodes on the top and bottom surfaces of the EAP 22, the EAP becomes thinner (T is less), and in order to conserve volume the area of the EAP expands as shown comparing panel B to panel A of FIG. 3.

Another type of field-activated EAP is electrostrictive graft elastomers, such as modified copolymer PVDF-TrFE (1). In these, application of an electric field causes charged pendant groups on the polymer to change their alignment, which shortens the polymer length. The response time of field-activated EAPs is very fast, much less than 1 second, which allows it to be used in the present application. Field-activated EAPs require high field strengths, as high as 200 V/micron.

Figure 4:
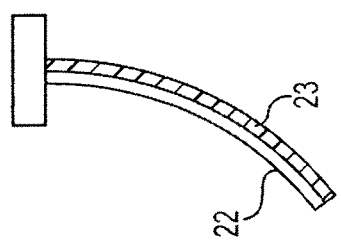
FIG. 4 shows movement of an ionic polymer metal composite with application of an electric field.
Figure 4:
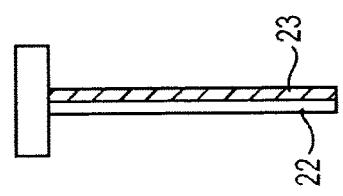

In other embodiments, the EAP is an ionic EAP (2). An example is Nafion (2). In one embodiment, the ionic EAP is formed as part of an ionic polymer-metal composite (2). The operation of these is shown in FIG. 3. EAP ionic polymer 22 is coated on one or both sides with a metal electroplated electrode 23. When an electrical charge is applied to the electrode 23, free counterions in the matrix of the EAP migrate toward (or away from) the electrode (depending on the polarity of the charge applied). This migration of the ions and their surrounding water molecules within the matrix of the ionic EAP causes the amount of matter on one side of the EAP to differ from the amount on the other side, and this causes the EAP to bend. This is shown in FIG. 4 panels A and B.

One limitation of ionic-polymer metal composites is a limited bending strain of only up to 3.3% (2).

In another embodiment, the ionic EAP is a conjugated polymer actuator, such as polyacetylene, polypyrole, polyaniline, and poly(3,4-ethylenedioxythiophene) (3). These are EAPs when they are in a partially oxidized state. Unlike other EAPs, these are also electrical conductors. They can be activated with a lower voltage than field-activated EAPs.

The EAP may more broadly be termed a contractomere. A "contractomere" is defined herein as a material that changes shape in response to application of an electric field. Some nonpolymeric materials are also contractomeres, in particular bistable rotaxanes, discussed below. In place of electroactive polymers, nonpolymeric contractomeres may also be used in the various embodiments of the present invention.

In one embodiment, the contractomere is an artificial molecular machine (4). An example is bistable rotaxanes, which are mechanically interlocked molecules that act much like actin and myosin do in natural muscles (4-6).

Some EAPs and other contractomeres are not able to recover quickly enough to perform 70 cycles per minute, i.e., approximately the rate of heart contraction. In that case, the contractomere may be stimulated to contract not on every beat, but every other or every third beat. That can provide enough assistance to the heart to slow or even reverse heart failure. Thus, in some embodiments, the device is adapted to electrically stimulate contraction of the contractomeres every other or every third time that the heart beats, or, where the device includes a pacemaker function (i.e., it includes electrodes that contact cardiac muscle and has the ability to pace beating of the heart), every other or every third time that the device paces the heart (i.e., its pacemaker function stimulates cardiac muscle to contract).

FIG. 1 shows one embodiment of a device of the invention. The device includes cardiac jacket 11 adapted to fit generally around at least a portion of the heart 99. Ribbons of sinusoidally shaped material 12 are included in the jacket 11 and circumscribe the ventricles of the heart. In one embodiment, the ribbons 12 are composed of electrically conductive material, such as nitinol on stainless steel, or an electrically conductive polymer. The ribbons 12 may be linked in the jacket by links 19, which may be nonelectrically conductive where it is desired to electrically isolate separate ribbons 12 from each other, or the links 19 may also be electrically conductive. Patches of EAP 22 are included in the jacket. The patches of EAP 22 link two segments of the ribbons 12. Upon contraction, the EAPs 22 contract the circumference of ribbons 12 about the heart to assist contraction of the heart. The EAPs 22 are shown linked by two electrical leads 13 to computerized generator 14. A battery 15 powers the generator 14. The generator applies an electric field to the EAPs 22 via leads 13 to expand or contract the EAPs 22.

In FIG. 2 another embodiment of the jacket 11 is shown. In this embodiment, the jacket 11 includes an electrically conductive material 12 arranged in a honeycomb-shaped pattern as a wrap that limits expansion of the heart. Because of the honeycomb-shaped pattern of the wrap, the wrap formed of material 12 has a fixed dimension and does not allow expansion of the heart beyond a certain dimension, unless the material 12 is elastic. The jacket 11 also includes bands 22 of EAP completely circumscribing the heart. One or more electrical leads 13 are applied to the EAPs 22 to link the EAPs to generator 14, which applies an electric field to the EAP to contract or expand the EAP. The embodiment shown in FIG. 2 also includes an inner liner 31. The inner line 31 may be seeded with stem cells. The inner line 31 may, for instance, be made of a polymer substrate for stem cell growth, such as polyurethane.

In one embodiment of the devices for treating cardiac disease, the device comprises (a) a cardiac jacket adapted to fit generally around at least a portion of the heart, the jacket comprising an electroactive polymer and the jacket having an inner surface in contact with the heart wall and an outer surface; and (b) stem cells adhering to or entrapped on the inner surface of the cardiac jacket.

The term "stem cells" as used herein refers to cells that are not fully differentiated. The stem cells can be pluripotent stem cells that can differentiate into any type of tissue, or multipotent stem cells that can differentiate into only certain tissues, such as cardiac or vascular tissues. Stem cells may also be unipotent stem cells that can only produce one cell type but have the property of self-renewal.

In one embodiment, the stem cells are umbilical cord stem cells.

In particular embodiments, the stem cells are smooth muscle cells or endothelial cells, or mixtures thereof (8). In other embodiments, the stem cells are purified adult uncommitted progenitor cells expressing the markers SSEA-1 and/or Oct-4 (U.S. patent publication no. 20070054397). In other embodiments, the stem cells are purified fetal blood multi-lineage progenitor cells positive for CD9 and CD45 (U.S. patent publication no. 20050255592). Methods to isolate, culture, and amplify the stem cells are described in U.S. patent publications nos. 20070054397 and 20050255592.

In other embodiments, the stem cells are bone marrow stem cells (13). In still other embodiments, the stem cells are myoblasts (14, 15). Both bone marrow stem cells and myoblasts can be autologous, i.e., isolated from the patient, as described in (13-15).

The stem cells are preferably adherent to or entrapped in the inner surface of the jacket. Thus, they can migrate more easily to the heart.

In particular embodiments, the inner surface of the jacket comprises a biodegradable polymer that entraps the stem cells. For instance, polylactic acid/polyglycolic acid copolymers and polyhydroxybutyrate are two suitable biodegradable polymers. In one embodiment, the jacket comprises a blend of polydioxanone and elastin (9). This is elastic, which is desirable since the jacket may change shape with contraction by the EAPs and stretching during diastole as the heart wall pushes against and expands the jacket. In other embodiments, the inner surface of the jacket comprises fibrin or collagen or a combination thereof. These natural materials are particularly biocompatible and promote cell growth.

In particular embodiments, the inner surface of the jacket comprises poly(carbonate-urea)urethane (8). This also is an elastic material.

In other embodiments, the inner surface of the jacket comprises a polymer that is not biodegradable.

With dielectric field-activated EAPs, applying a charge to electrodes on opposite surfaces of the EAP causes the EAP to become thinner, which in turn lengthens the EAP to conserve the total volume. In this case the EAP preferably contacts an inner surface electrode and an outer surface electrode. Applying a voltage across the two electrodes causes the EAP to expand in area. This is shown in FIG. 3. If the EAP is prestrained in a first dimension, it will expand preferentially in a second dimension perpendicular to the first dimension and perpendicular to the activating electric field (10). Thus, if the EAP in the jacket is prestrained in a dimension along the vertical axis of the heart, it will preferentially expand and contract along the lateral dimension of the heart.

Thus, in one embodiment, the electroactive polymer contacts toward the inner surface of the jacket an inner surface electrically conductive layer formed of the electrically conductive material and contacts toward the outer surface of the jacket an outer surface electrically conductive layer formed of the electrically conductive material.

The cardiac jacket typically is a mesh—that is, it includes perforations. This makes it easier for the jacket to fit the contours of the heart without folds. In some embodiments, some material of the cardiac jacket is in the form of a honeycomb (i.e., hexagonal shaped mesh pattern) (FIG. 2). In other embodiments, the jacket does not contain any perforations. This maximizes the surface area of the jacket in contact with the heart, which is useful if the inner surface of the jacket includes stem cells for delivery to the heart, and where the jacket includes electrically conductive material and is used to apply an electromagnetic field to the surface of the heart to stimulate tissue growth or differentiation in the heart.

Where the jacket includes electrically conductive material, the device may comprise electrical leads linking the generator and the electrically conductive material. The electrically conductive material may serve as one or more electrodes for the EAP. The electrically conductive material may also serve as electrodes to establish an electromagnetic field at the surface of the heart effective to promote growth and differentiation of stem cells into cardiac tissue or to promote growth and differentiation of cardiac tissue.

To promote growth and differentiation of cardiac tissue, in some embodiments, electrical current (electric field) is delivered in pulses at a rate between 50 and 90 pulses per minute to the electrically conductive material of the jacket. In other embodiments, the electric current (electric field) to promote tissue growth is continuous. In other embodiments, the electric current (electric field) is delivered with a frequency of approximately 5 to 100 Hz. For instance, it may be delivered as alternating current with a frequency of 5 to 100 Hz, or as direct current in pulses of 5 to 100 pulses per second.

In some embodiments, the electromagnetic field is concentrated over a specific area of the heart. It may, for instance, be concentrated over an infarct in the heart. In other embodiments, the electromagnetic field is concentrated over the left ventricle. Concentration of the electromagnetic field over a specific area of the heart may be achieved by distributing the electrically conductive material in the cardiac jacket unequally, so it is concentrated in a particular area of the jacket. It may also be achieved with a symmetrical arrangement of the electrically conductive material by delivering the electrical charge to only some of the electrically conductive material—i.e., only that over the specific area of the heart that is targeted.

In other embodiments, the electromagnetic field is distributed evenly over the majority of the heart. In these embodiments, for instance, the cardiac jacket may comprise electrically conductive material distributed evenly over the majority of the area of the cardiac jacket, and the electric current may be applied evenly over all of the electrically conductive material of the jacket to distribute the applied electromagnetic field substantially evenly over the majority or all of the surface area of the heart.

Several embodiments of the devices and methods described herein involve a generator is adapted to deliver an electric potential or electric current to the electrically conductive material to establish an electromagnetic field at the surface of the heart effective to promote growth of cardiac tissue. The electromagnetic field may be an electric field or a magnetic field. In particular embodiments, the electric potential or electric current is continuous. In other embodiments the electric potential or electric field is delivered in pulses at a rate of between 40 and 120 pulses per minute. In other embodiments, the electric current is delivered as alternating current with a frequency of approximately 5 to 100 Hz.

The applied electric field to promote growth or differentiation of stem cells or cardiac tissue may be any field strength determined to promote growth or differentiation. In particular embodiments, it is 1 mV to 2 V. In specific embodiments, it is 20 mV to 0.5 V. In particular embodiments, it is 20 mV to 0.3 V (11, 12).

Several embodiments of the invention involve delivering stem cells to the heart. Stem cells may be adherent to or entrapped on the inner surface of the cardiac jacket, and delivered to the heart by implanting the jacket.

In other embodiments, the stem cells are delivered by injecting stem cells into the wall of the heart of the patient.

In specific embodiments, the stem cells are delivered during transmyocardial revascularization (TMR). In TMR a $CO_2$ laser is used to create typically 20 to 40 1-mm-wide channels through the wall of the heart, typically the left ventricle. TMR improves blood flow to the wall of the heart, apparently in two ways. First, the exterior of the channels appears to seal and blood flows directly into the channels from the interior of the heart. Second, TMR appears to promote angiogenesis—new capillary growth near the channels.

It is beneficial to deliver stem cells to the heart through the channels created in TMR. Thus, in one embodiment of the methods of the invention, the method comprises drilling a plurality of channels through a wall of the heart; and the step of delivering stem cells comprises placing stem cells in the channels.

One embodiment of the invention provides a device for treating cardiac disease comprising: (a) a cardiac jacket adapted to fit generally around at least a portion of the heart, the jacket comprising an electrically conductive material and one or more bladders adapted for dilation and contraction in response to varying fluid pressure therewithin; (b) a fluid pump; (c) one or more conduits connecting the one or more bladders and the fluid pump; wherein the one or more bladders are adjacent a pumping chamber of the heart to exert varying mechanical pressure on a region of the pumping chamber of the heart with dilation and contraction of the one or more bladders; and (d) a generator electrically linked by one or more electrical leads to the electrically conductive material of the cardiac jacket; wherein the generator is adapted to deliver an electric potential or electric current to the electrically conductive material to establish an electromagnetic field at the surface of the heart effective to promote growth of cardiac tissue.

Figure 5:
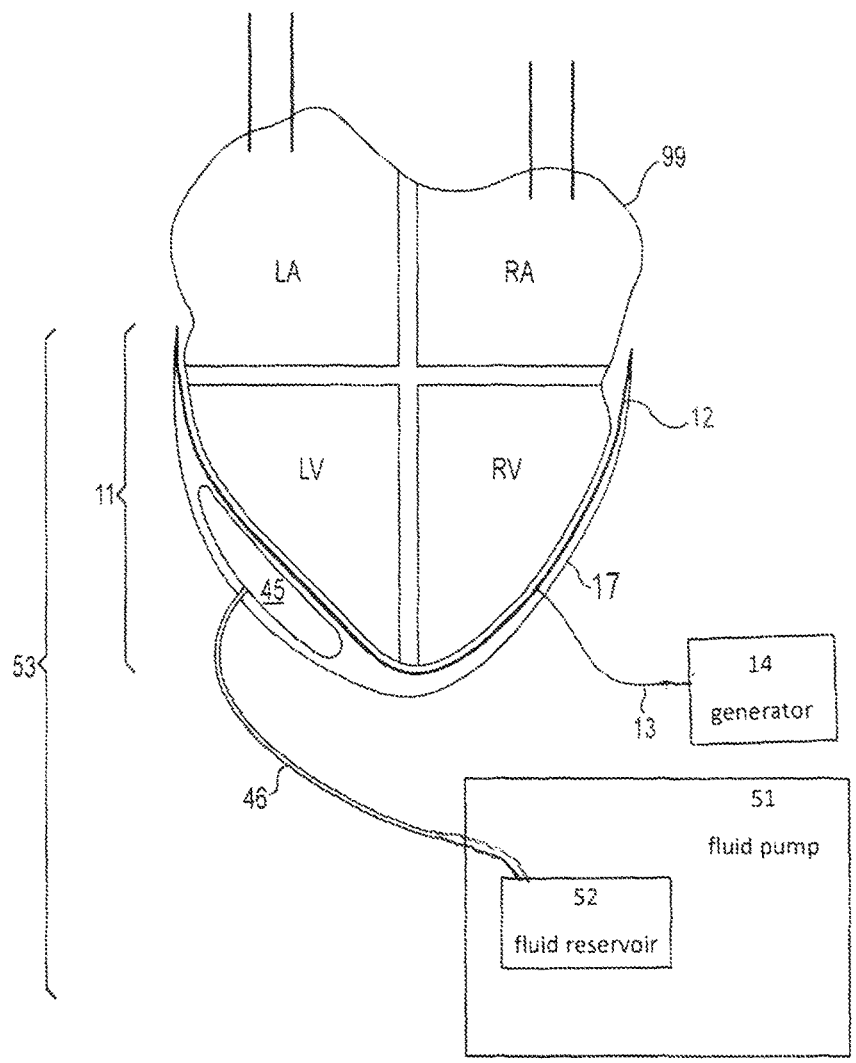
FIG. 5 is a cross-sectional view of the heart and a device of the invention for treating cardiac disease that includes a hydraulic bladder in a cardiac jacket external to the heart.

FIG. 5 shows such a device 53. It includes jacket 11 with bladder 45 located between a restraint 17. The restraint 17 may be, for instance, an elastic jacket or cup or a jacket or cup that is of fixed dimensions to prevent expansion when the bladder 45 expands. An inner layer 12 composed of electrically conductive material is shown. The electrically conductive material 12 is linked by electrical lead 13 to generator 14. The bladder 45 is shown in FIG. 5 positioned against the wall of the left ventricle (LV). In other embodiments it may wrap about the entire heart or both ventricles, or may be positioned against and selectively compress another pumping chamber of the heart. Conduit 46 is shown linking bladder 45 to fluid pump 51. The fluid pump 51 is shown as including a fluid reservoir 52.

The bladders can be selectively positioned and constrained to apply pressure selectively to only part of the heart. For instance, the bladders can be positioned to selectively apply pressure to the left ventricle, which is usually the primary chamber that needs assistance in heart failure. They also may apply pressure selectively to the lower portion of the left ventricle to assist contraction in a particular direction. Thus, in one embodiment, at least one of the bladders is positioned adjacent to one pumping chamber (e.g., the left ventricle); wherein the device exerts greater pressure on the pumping chamber to which it is adjacent in systole than the other pumping chambers of the heart.

Another embodiment of the invention provides a device for treating cardiac disease comprising: a cardiac jacket adapted to fit generally around at least a portion of the heart, the jacket comprising an elastic or contractile material such that the jacket expands with diastole of the heart and contracts with systole of the heart around at least one pumping chamber of the heart; the cardiac jacket comprising at least two dimensional transducer elements; electrically coupled to a monitor; wherein the transducer elements are adapted to measure signals that allow determination of distance between the at least two transducer elements and are adapted to transmit the signals to the monitor. The transducer elements are coupled to material of the cardiac jacket such that as the jacket expands or contracts with the beating of the heart and/or contraction of the jacket by forces external to the heart, e.g., forces generated by a contractomere in the jacket, the transducer elements move with the material of the jacket and the distance between the transducer elements is monitored. The distance is an indicator of how much the jacket contracts or expands and how much the heart contracts and expands. Thus, the measurements can be used to monitor heart function across time. The measurements can be used, for instance, to give an estimate of ejection fraction. They can also show enlargement of the heart or reversal of enlargement over time.

Dimensional transducers are known in the art. Suitable dimensional transducers are disclosed for instance in U.S. Pat. No. 7,307,374 and U.S. Pat. No. 5,438,998.

FIG. 2 shows a jacket 11 that includes dimensional transducer elements 41 that are coupled to a band 22 of electroactive polymer. As the EAP contracts and expands and the heart contracts and expands to contract and expand the jacket and the circumference of band 22, the distance between the dimensional transducer elements 41 changes and this can be monitored to monitor heart function and/or the function of the jacket.

Another embodiment provides a method of monitoring heart function comprising: monitoring variation of distance between at least two dimensional transducer elements coupled to a cardiac jacket adapted to fit generally around at least a portion of a heart, the jacket comprising an elastic or contractile material such that the jacket expands with diastole of the heart and contracts with systole of the heart around at least one pumping chamber of the heart.

REFERENCES

1. Bar-Cohen, Y. et al., 2008, Electroactive polymer actuators and sensors. *MRS Bulletin* 33:173-117.
2. Park, I-S. et al., 2008, Physical principles of ionic polymer-metal composites as electroactive actuators and sensors. *MRS Bulletin* 33:190-195.
3. Smela, E., 2008, Conjugated polymer actuators. *MRS Bulletin* 33:197-204.
4. Huang, T. J., 2008, Recent developments in artificial molecular-machine-based active nanomaterials and nanosystems. *MRS Bulletin* 33:226-231.
5. Balzani, V. et al. 1998. *Acc. Chem. Res.* 31:405.
6. Balzani, V. et al., 2000, *Agnew. Chem. Int. Ed.* 39:3348.
7. Kelly, T. R., 1999, *Nature* 401:150.
8. Rashid, S. T. et al. 2008. Tissue engineering of a hybrid bypass graft for coronary and lower limb bypass surgery. *FASEB Journal* 22:2084-2089.
9. Smith, M. J. et al. 2008 In vitro evaluations of innate and acquired immune responses to electrospun polydioxanone-elastin blends. *Biomaterials.* 2008 Oct. 11.
10. Perline, R. et al., 2000, High-speed electrically actuated elastomers with strain greater than 100%. *Science* 287: 836-839.
11. Kanno, S. et al., 1999, Establishment of a simple and practical procedure applicable to therapeutic angiogenesis. *Circulation* 99:2692-2687.
12. Zhao, M. et al. 2003, Electrical stimulation directly induces pre-angiogenic responses in vascular endothelial cells by signaling through VEGF receptors. *J. Cell Science* 117:397-405.
13. Thompson, R. B. et al. 2005. Intracardiac transplantation of a mixed population of bone marrow cells improves both regional systolic contractility and diastolic relaxation. *J. Heart Lung Transplantation* 24:205-214.
14. Taylor, D. A. et al. 1997. Delivery of primary autologous skeletal myoblasts into rabbit heart by coronary infusion: a potential approach to myocardial repair. *Proc. Assoc. American Physicians* 109:245-253.
15. Taylor, D. A. et al. 1998. Regenerating functional myocardium: improved performance after skeletal myoblast transplantation. *Nature Med.* 4:929-933.

All patents, patent documents, and other references cited herein are incorporated by reference.

STATEMENTS OF THE INVENTION

1. A device for treating cardiac disease comprising:
   a cardiac jacket adapted to fit generally around at least a portion of the heart, the jacket comprising an electroactive polymer, wherein the electroactive polymer switches between a longer and shorter state in response to electrical activation; wherein the electroactive polymer is arranged in the jacket such that when the electroactive polymer is in the shorter state it contracts circumference of the cardiac jacket about the heart so as to assist contraction of one or more pumping chambers of the heart; the jacket having an inner surface in contact with the heart wall and an outer surface; and
   stem cells adhering to or entrapped on the inner surface of the cardiac jacket.
2. The device of statement 1 further comprising:
   a computerized generator electrically linked by
   one or more electrical leads to
   the electroactive polymer of the cardiac jacket.
3. The device of statement 2 further comprising a battery electrically coupled to the computerized generator.
4. The device of statement 2 or 3 further comprising one or more sensing electrodes electrically coupled to the heart and electrically coupled to the computerized generator; wherein the device is adapted to detect the contraction rhythm of the heart with the sensing electrodes and to generate electrical pulses effective to contract the electroactive polymer with the computerized generator at a variable rate responsive to physiological activity of the patient.
5. The device of statement 1 wherein the cardiac jacket comprises:
   electrically conductive material
6. The device of statement 5 wherein the electrically conductive material is linked electrically and mechanically to the electroactive polymer.
7. The device of statement 5 wherein the electrically conductive material is formed into one or more sinusoidally shaped strands arranged laterally on the heart, wherein the electroactive polymer links portions of the same or different sinusoidally shaped strands.
8. The device of statement 7 wherein the strands of electrically conductive material form one or more bands completely circumscribing the heart.
9. The device of statement 7 wherein the electroactive polymer is a field-activated polymer, e.g., PVDF or VHB 4910.
10. The device of statement 1 wherein when the device is implanted in a patient, the stem cells of the inner surface of the jacket grow into a tissue that adheres the jacket to the wall of the heart.

11. The device of statement 1 wherein the inner surface comprises a biodegradable polymer matrix that entraps the stem cells.
12. The device of statement 11 wherein inner surface of the jacket comprises a blend of polydioxanone and elastin.
13. The device of statement 1 or 11 wherein the inner surface comprises fibrin or collagen or a combination thereof.
14. The device of statement 1 wherein the inner surface comprises poly(carbonate-urea)urethane.
15. The device of statement 5 wherein the electroactive polymer contacts toward the inner surface of the jacket an inner surface electrically conductive layer formed of the electrically conductive material and contacts toward the outer surface of the jacket an outer surface electrically conductive layer formed of the electrically conductive material.
16. The device of statement 5 wherein the generator is adapted to deliver an electric potential or an electric current to the electrically conductive material to establish an electromagnetic field at the surface of the heart effective to promote growth and differentiation of the stem cells into cardiac tissue.
17. The device of statement 1 wherein the device is adapted to adhere to the heart wall through tissue grown from the stem cells after implantation in a patient.
18. The device of statement 1 wherein the stem cells are purified adult uncommitted progenitor cells expressing the markers SSEA-1 and/or Oct-4 [US 20070054397.
19. The device of statement 1 wherein the stem cells are purified fetal blood multi-lineage progenitor cells positive for CD9 and CD45. [US 20050255592].
20. The device of statement 5 wherein the device comprises electrical leads electrically linking the generator and the electrically conductive material.
21. The device of statement 2 further comprising one or more electrical leads linking the generator to
one or more electrodes contacting cardiac muscle of one or more pumping chambers of the heart to pace pumping of the heart muscle.
22. The device of statement 21 wherein the device comprises electrical leads linking the generator to an electrode contacting cardiac muscle of the left ventricle and an electrode contacting cardiac muscle of the right ventricle to coordinately pace both ventricles.
23. The device of statement 2 further comprising an implantable cardioverter defibrillator comprising:
a capacitor for storing electrical charge, linked by
electrical leads to
at least two electrodes contacting tissue, wherein at least one of the electrodes contacts cardiac tissue.
24. A method of treating cardiac disease comprising:
implanting in a patient a cardiac jacket adapted to fit generally around at least a portion of the heart, the jacket comprising an electroactive polymer, wherein the electroactive polymer switches between a longer and shorter state in response to electrical activation; wherein the electroactive polymer is arranged in the jacket such that when the electroactive polymer is in the shorter state it contracts circumference of the cardiac jacket about the heart so as to assist contraction of one or more pumping chambers of the heart; and delivering stem cells to the heart of the patient.
25. A method of treating cardiac disease comprising:
implanting in a patient a cardiac jacket adapted to fit generally around at least a portion of the heart, the jacket comprising electrically conductive material;
electrically linking the electrically conductive material of the cardiac jacket to a generator;
wherein the generator is adapted to deliver an electric potential or an electric current to the electrically conductive material to establish an electromagnetic field at the surface of the heart effective to promote growth and differentiation of the stem cells into cardiac tissue.
26. The method of statement 25 further comprising delivering an electric current with the generator in pulses at a rate between 40 and 120 pulses per minute to the electrically conductive material to establish an electromagnetic field at the surface of the heart effective to promote growth and differentiation of cardiac tissue.
27. The method of statement 25 further comprising delivering stem cells to the heart of the patient.
28. The method of statement 27 wherein the jacket has an inner surface in contact with the heart wall and an outer surface and wherein the jacket further comprises stem cells adhering to or entrapped on the inner surface of the cardiac jacket; wherein the step of delivering stem cells to the heart comprises implanting the jacket.
29. The method of statement 27 wherein the step of delivering stem cells comprises injecting stem cells into the wall of the heart of the patient.
30. The method of statement 26 wherein the method further comprises drilling a plurality of channels through a wall of the heart; and the step of delivering stem cells comprises placing stem cells in the channels.
31. A device for treating cardiac disease comprising:
a cardiac jacket adapted to fit generally around at least a portion of the heart, the jacket comprising electrically conductive material;
a generator electrically linked by
electrical leads to
the electrically conductive material of the cardiac jacket;
wherein the generator is adapted to deliver an electric potential or an electric current to the electrically conductive material to establish an electromagnetic field at the surface of the heart effective to promote growth and differentiation of the stem cells into cardiac tissue.
31b. The device of statement 31 wherein the jacket is sized to restrain expansion of the heart in diastole.
32. The device of statement 31 wherein the electromagnetic field is concentrated over an area of an infarct in the heart.
33. The device of statement 31 wherein the cardiac jacket comprises an electroactive polymer linked by electrical leads to the generator wherein the electroactive polymer is adapted to contract in the device at a frequency of 40 to 120 contractions per minute to contract the left ventricle of the heart.
34. A device for treating cardiac disease comprising:
a cardiac jacket adapted to fit generally around at least a portion of the heart, the jacket comprising an electrically conductive material and one or more bladders adapted for dilation and contraction in response to varying fluid pressure therewithin;
a fluid pump;
one or more conduits connecting the one or more bladders and the fluid pump; wherein the one or more bladders are adjacent a pumping chamber of the heart to exert varying mechanical pressure on a region of the pumping chamber of the heart with dilation and contraction of the one or more bladders;
a generator electrically linked by one or more electrical leads to the electrically conductive material of the cardiac jacket;

wherein the generator is adapted to deliver an electric potential or an electric current to the electrically conductive material to establish an electromagnetic field at the surface of the heart effective to promote growth and differentiation of the stem cells into cardiac tissue.

34a. The device of statement 34 wherein the generator is adapted to deliver an electrical current in pulses at a rate between 40 and 120 pulses per minute to the electrically conductive material to establish an electromagnetic field at the surface of the heart effective to promote growth of cardiac tissue.

35. The device of statement 34 wherein at least one of the bladders is positioned adjacent to the left ventricle; wherein the device selectively exerts greater pressure on the left ventricle in systole than the other pumping chambers of the heart.

36. A device for treating cardiac disease comprising:
a cardiac jacket adapted to fit generally around at least a portion of the heart, the jacket comprising an elastic or contractile material such that the jacket expands with diastole of the heart and contracts with systole of the heart around at least one pumping chamber of the heart;
the cardiac jacket comprising at least two dimensional transducer elements; electrically coupled to
a monitor;
wherein the transducer elements are adapted to measure signals that allow determination of distance between the at least two transducer elements and are adapted to transmit the signals to the monitor.

37. A method of monitoring heart function comprising:
monitoring variation of distance between at least two dimensional transducer elements coupled to a cardiac jacket adapted to fit generally around at least a portion of a heart, the jacket comprising an elastic or contractile material such that the jacket expands with diastole of the heart and contracts with systole of the heart around at least one pumping chamber of the heart.

38. The method of statement 37 wherein the jacket comprises a contractile material that is an electroactive polymers, wherein the electroactive polymer switches between a longer and shorter state in response to electrical activation; wherein the electroactive polymer is arranged in the jacket such that when the electroactive polymer is in the shorter state it contracts circumference of the cardiac jacket about the heart so as to assist contraction of one or more pumping chambers of the heart;
wherein the electroactive polymer is electrically linked to a computerized generator by one or more electrical leads, and the computerized generator delivers a voltage to the electroactive polymer;
the method further comprising altering the voltage delivered to the electroactive polymer to alter magnitude of contraction of the electroactive polymer in response to the variation of distance between the at least two transducer elements.

38b. The method of claim 38 wherein the method comprises altering the voltage delivered to the electroactive polymer a plurality of times in response to changes in the variation of distance between the at least two transducer elements.

39. The method of statement 37 wherein the jacket comprises a contractile material that is one or more bladders adapted for dilation and contraction in response to varying fluid pressure therewithin; and the jacket further comprises a fluid pump in fluid communication with the bladders and adapted to vary the pressure in each of the one or more bladders between a maximum pressure and a minimum pressure; and
one or more conduits connecting the one or more bladders and the fluid pump; wherein the one or more bladders are adjacent a pumping chamber of the heart to exert varying mechanical pressure on a region of the pumping chamber of the heart with dilation and contraction of the one or more bladders;
the method further comprising changing the maximum pressure in at least one of the one or more bladders and thereby changing the mechanical pressure on a region of the pumping chamber of the heart in response to the variation in distance between the at least two transducer elements.

40. The method of statement 39 wherein the method comprises changing the maximum pressure in at least one of the one or more bladders a plurality of times in response to changes in the variation in distance between the at least two transducer elements.

What is claimed is:

1. A device for treating cardiac disease comprising:
a cardiac jacket adapted to fit generally around at least a portion of a heart, the jacket comprising a contractile material such that the jacket expands with diastole of the heart and contracts with systole of the heart around at least one pumping chamber of the heart;
the cardiac jacket comprising at least two dimensional transducer elements; electrically coupled to
a monitor;
wherein the transducer elements are adapted to measure signals that allow determination of distance between the at least two transducer elements and are adapted to transmit the signals to the monitor;
wherein the contractile material is one or more bladders adapted for dilation and contraction in response to varying fluid pressure therewithin; and the jacket further comprises
a fluid pump in fluid communication with the bladders and adapted to vary the pressure in each of the one or more bladders between a maximum pressure and a minimum pressure; and
one or more conduits connecting the one or more bladders and the fluid pump;
wherein the one or more bladders are adjacent a pumping chamber of the heart to exert varying mechanical pressure on a region of the pumping chamber of the heart with dilation and contraction of the one or more bladders;
wherein the one or more bladders selectively positioned and constrained to apply pressure selectively to the left ventricle or to the right ventricle of the heart;
wherein the device does not comprise a restraint outside of the bladders that is of fixed dimensions to prevent expansion of the bladders.

2. The device of claim 1 wherein the jacket has an inner surface in contact with a heart wall and an outer surface; and
stem cells adhering to or entrapped on the inner surface of the cardiac jacket.

3. The device of claim 2
wherein the cardiac jacket comprises an electrically conductive material;
wherein the device further comprises a generator electrically linked by electrical leads to the electrically conductive material of the cardiac jacket; wherein the generator is adapted to deliver an electric potential or an electric current to the electrically conductive material to establish an electromagnetic field at the surface of the heart effective to promote growth of cardiac tissue.

4. The device of claim 3 wherein the electromagnetic field is concentrated over an area of an infarct in the heart.

5. The device of claim 1
wherein the cardiac jacket comprises an electrically conductive material and one or more bladders adapted for dilation and contraction in response to varying fluid pressure therewithin;
wherein the device further comprises a generator electrically linked by electrical leads to the electrically conductive material of the cardiac jacket; wherein the generator is adapted to deliver an electric potential or an electric current to the electrically conductive material to establish an electromagnetic field at the surface of the heart effective to promote growth of cardiac tissue.

6. The device of claim 5 wherein the generator is adapted to deliver an electric potential or an electric current to the electrically conductive material in pulses at a rate of 40 to 120 pulses per minute to establish an electromagnetic field at the surface of the heart effective to promote growth of cardiac tissue.

7. The device of claim 1 wherein the one or more bladders are selectively positioned and constrained to apply pressure selectively to the left ventricle only, and no bladders are positioned to apply pressure to the right ventricle.

8. The device of claim 1 wherein the one or more bladders are selectively positioned and constrained to apply pressure selectively to the right ventricle only, and no bladders are positioned to apply pressure to the left ventricle.

9. The device of claim 1 wherein the contractile material is two or more bladders, and one or more of the two or more bladders are selectively positioned and constrained to apply pressure selectively to the left ventricle only and one or more of the two or more bladders are selectively positioned and constrained to apply pressure selectively to the right ventricle only.

10. The device of claim 1 wherein the device does not comprise a restraint outside of the bladders that restrains outward expansion of the bladders.

* * * * *

UNITED STATES PATENT AND TRADEMARK OFFICE
CERTIFICATE OF CORRECTION

PATENT NO. : 10,220,128 B1
APPLICATION NO. : 12/590378
DATED : March 5, 2019
INVENTOR(S) : Allan R. Robinson et al.

Page 1 of 1

It is certified that error appears in the above-identified patent and that said Letters Patent is hereby corrected as shown below:

In the Claims

Line 29 of Claim 1 (Column 16, Line 51) should read:
--wherein the one or more bladders are selectively positioned--

Signed and Sealed this
Seventh Day of May, 2019

Andrei Iancu
*Director of the United States Patent and Trademark Office*